United States Patent
Tegg et al.

(10) Patent No.: US 9,943,408 B2
(45) Date of Patent: Apr. 17, 2018

(54) BASKET DELIVERY SYSTEM

(71) Applicant: St. Jude Medical, Cardiology Division, Inc., St. Paul, MN (US)

(72) Inventors: Troy Tegg, Elk River, MN (US); Jacob John Daly, Blaine, MN (US); Aaron J. Chalekian, Savage, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 422 days.

(21) Appl. No.: 14/590,271

(22) Filed: Jan. 6, 2015

(65) Prior Publication Data
US 2015/0190230 A1    Jul. 9, 2015

Related U.S. Application Data

(60) Provisional application No. 61/924,786, filed on Jan. 8, 2014.

(51) Int. Cl.
*A61F 2/24* (2006.01)
*A61F 2/966* (2013.01)
*A61F 2/95* (2013.01)

(52) U.S. Cl.
CPC ............ *A61F 2/2436* (2013.01); *A61F 2/966* (2013.01); *A61F 2002/9517* (2013.01);
(Continued)

(58) Field of Classification Search
CPC . A61F 2/2436; A61F 2/966; A61F 2002/9517
(Continued)

(56) References Cited

U.S. PATENT DOCUMENTS

| 3,657,744 A | 4/1972 | Ersek |
| 4,423,730 A | 1/1984 | Gabbay |

(Continued)

FOREIGN PATENT DOCUMENTS

| EP | 1129744 A1 | 9/2001 |
| EP | 1157673 A2 | 11/2001 |

(Continued)

OTHER PUBLICATIONS

Extended European Search Report for Application No. 15150273.9 dated May 22, 2015.
(Continued)

*Primary Examiner* — Diane Yabut
*Assistant Examiner* — Martin T Ton
(74) *Attorney, Agent, or Firm* — Lerner, David, Littenberg, Krumholz & Mentlik, LLP

(57) ABSTRACT

A delivery device for a collapsible medical device may include a handle and a delivery assembly having a compartment for receiving the medical device. A catheter member may extend from the handle to the delivery assembly. The catheter member may have a first portion with a first compliance value and a second portion with a second compliance value different from the first compliance value. An internally threaded member may be fixedly connected to the delivery assembly. An externally threaded member may have a first portion operatively connected to the actuation member and a second portion threadedly coupled to the internally threaded member so that manipulation of the actuation member causes axial movement of the compartment relative to the catheter member.

8 Claims, 7 Drawing Sheets

(52) U.S. Cl.
CPC ............... *A61F 2220/0025* (2013.01); *A61F 2250/0008* (2013.01); *A61F 2250/0018* (2013.01); *A61F 2250/0029* (2013.01)

(58) Field of Classification Search
USPC .............................................. 623/1.11, 2.11
See application file for complete search history.

(56) References Cited

U.S. PATENT DOCUMENTS

| | | | |
|---|---|---|---|
| 5,843,167 | A | 12/1998 | Dwyer et al. |
| 5,924,424 | A | 7/1999 | Stevens et al. |
| 5,968,068 | A | 10/1999 | Dehdashtian et al. |
| 6,077,297 | A | 6/2000 | Robinson et al. |
| 6,306,141 | B1 | 10/2001 | Jervis |
| 6,623,518 | B2 | 9/2003 | Thompson et al. |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,311,730 | B2 | 12/2007 | Gabbay |
| 7,510,572 | B2 | 3/2009 | Gabbay |
| 7,682,390 | B2 | 3/2010 | Seguin |
| 7,803,185 | B2 | 9/2010 | Gabbay |
| 8,172,792 | B2 * | 5/2012 | Wang ................. A61F 2/958 604/101.03 |
| 2003/0050694 | A1 | 3/2003 | Yang et al. |
| 2004/0210304 | A1 | 10/2004 | Seguin et al. |
| 2005/0137695 | A1 | 6/2005 | Salahieh et al. |
| 2005/0137697 | A1 | 6/2005 | Salahieh et al. |
| 2006/0074484 | A1 | 4/2006 | Huber |
| 2006/0106415 | A1 | 5/2006 | Gabbay |
| 2006/0142848 | A1 | 6/2006 | Gabbay |
| 2006/0167468 | A1 | 7/2006 | Gabbay |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0055358 | A1 | 3/2007 | Krolik et al. |
| 2007/0073391 | A1 | 3/2007 | Bourang et al. |
| 2007/0088431 | A1 | 4/2007 | Bourang et al. |
| 2007/0112422 | A1 | 5/2007 | Dehdashtian |
| 2007/0162100 | A1 | 7/2007 | Gabbay |
| 2007/0168013 | A1 | 7/2007 | Douglas |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2008/0071369 | A1 | 3/2008 | Tuval et al. |
| 2008/0114435 | A1 * | 5/2008 | Bowe ................. A61F 2/95 623/1.11 |
| 2008/0147182 | A1 | 6/2008 | Righini et al. |
| 2009/0054975 | A1 | 2/2009 | del Nido et al. |
| 2009/0105801 | A1 * | 4/2009 | Ivancev ................. A61F 2/954 623/1.11 |
| 2009/0254165 | A1 | 10/2009 | Tabor et al. |
| 2010/0004740 | A1 | 1/2010 | Seguin et al. |
| 2010/0049313 | A1 * | 2/2010 | Alon ................. A61F 2/2418 623/2.11 |
| 2010/0286768 | A1 | 11/2010 | Alkhatib |
| 2010/0298931 | A1 | 11/2010 | Quadri et al. |
| 2011/0224678 | A1 | 9/2011 | Gabbay |
| 2012/0078351 | A1 * | 3/2012 | Klima ................. A61F 2/2436 623/2.11 |
| 2013/0123757 | A1 * | 5/2013 | Crisostomo ............ A61B 17/00 606/1 |

FOREIGN PATENT DOCUMENTS

| | | |
|---|---|---|
| EP | 1926455 A2 | 6/2008 |
| WO | 2004060442 A2 | 7/2004 |
| WO | 07071436 A2 | 6/2007 |
| WO | 08070797 A2 | 6/2008 |
| WO | 2010022138 A2 | 2/2010 |
| WO | 10051025 A1 | 5/2010 |
| WO | 10087975 A1 | 8/2010 |
| WO | 2012036741 A2 | 3/2012 |
| WO | 2012116368 A2 | 8/2012 |
| WO | 2013082583 A1 | 6/2013 |
| WO | 2013167458 A1 | 11/2013 |

OTHER PUBLICATIONS

Quaden, René et al., "Percutaneous aortic valve replacement: resection before implantation," 836-840, European J. of Cardio-thoracic Surgery 27 (2005).

Ruiz, Carlos, "Overview of PRE-CE Mark Transcatheter Aortic Valve Technologies", Euro PCR, May 25, 2010.

* cited by examiner

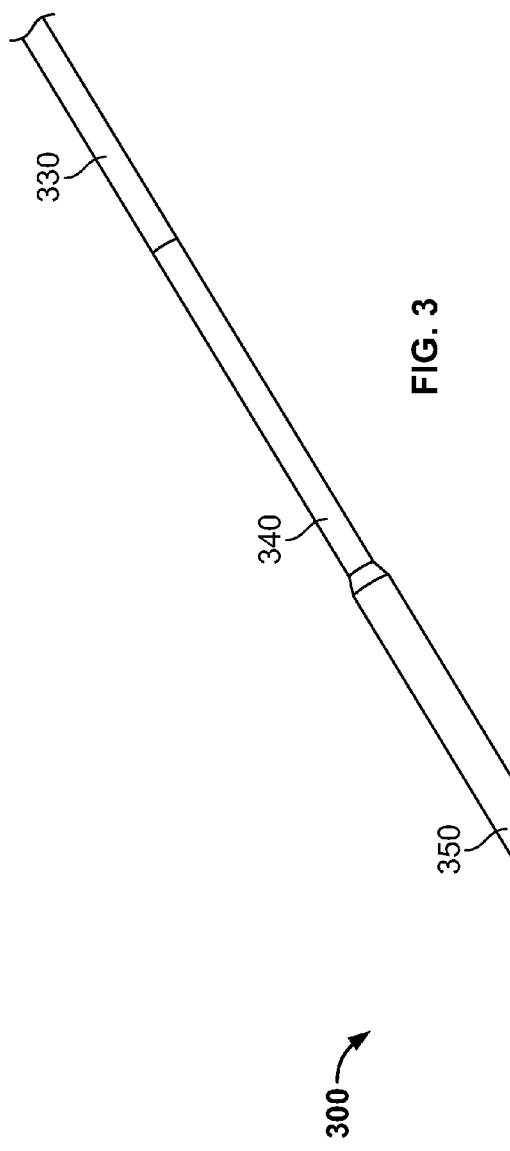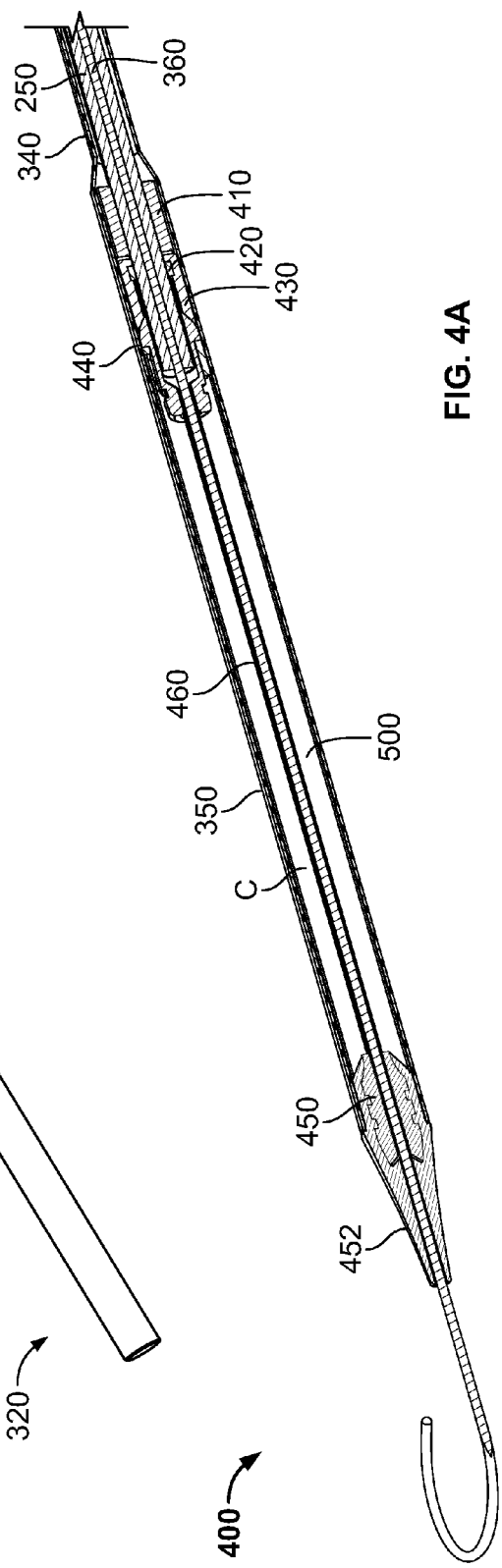

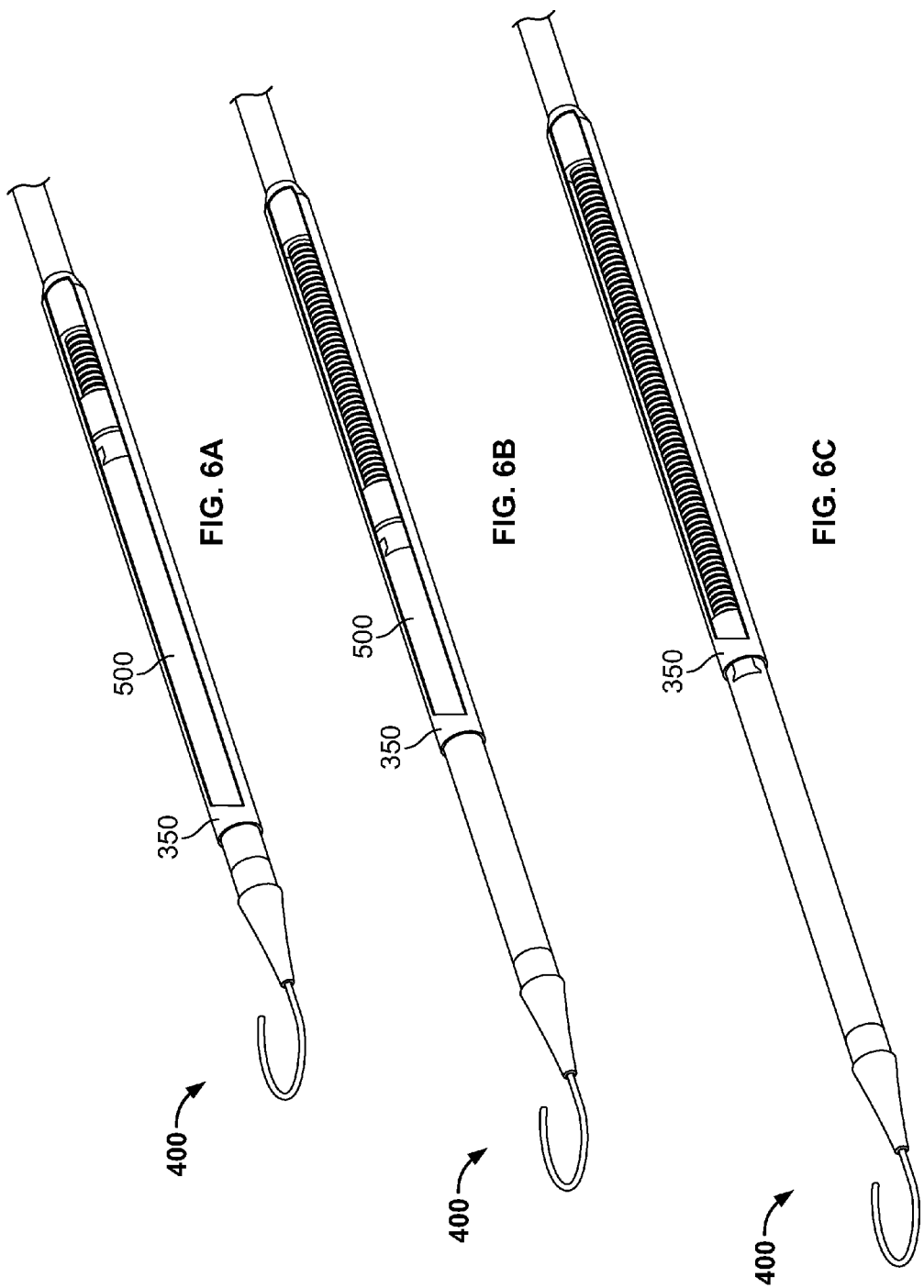

BASKET DELIVERY SYSTEM

CROSS-REFERENCE TO RELATED APPLICATIONS

This application claims the benefit of the filing date of U.S. Provisional Patent Application No. 61/924,786 filed Jan. 8, 2014, the disclosure of which is hereby incorporated by reference herein.

BACKGROUND

The present disclosure is related to prosthetic heart valve replacement, and more particularly to devices, systems, and methods for delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, generally the valve is first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the outer sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheathes the annulus end of the valve, so that the valve can be repositioned while in a collapsed state. After the valve has been repositioned, the user can again release the valve.

In traditional deployment methods, the user operates a handle to cause distal or proximal movement of a catheter or other member within the handle, resulting in relative movement between the prosthetic valve and an outer sheath covering the prosthetic valve so as to cause deployment of the valve. For example, in a typical transfemoral delivery device, a distal end of an outer sheath surrounds the prosthetic valve, and a proximal end of the outer sheath may be fixed to a carriage within the handle. Manipulation of the handle causes the carriage to move proximally or distally, which in turn causes proximal or distal movement of the outer sheath. In a typical transapical delivery device, a distal end of an inner shaft may support the prosthetic valve, and a proximal end of the inner shaft may be attached to a carriage within the handle, while the outer sheath may be fixedly connected at its proximal end to the handle. Manipulation of the handle causes the carriage to move proximally or distally, which in turn causes proximal or distal movement of the inner shaft relative to the outer sheath. In both examples above, manipulation of the delivery device handle causes proximal or distal movement of a carriage, which movement is translated along most or all of the length of the device, through either the outer sheath or inner shaft.

BRIEF SUMMARY

According to one embodiment of the present disclosure, a delivery device for a collapsible medical device may include a handle having an actuation member; a delivery assembly having a compartment for receiving the medical device; a catheter member extending from the handle to the delivery portion; an internally threaded member fixedly connected to the delivery assembly; and an externally threaded member having a first portion operatively connected to the actuation member and a second portion threadedly coupled to the internally threaded member so that manipulation of the actuation member causes axial movement of the compartment relative to the catheter member.

According to another embodiment of the present disclosure, a delivery device for a collapsible medical device may include a handle; a delivery assembly having a compartment for receiving the medical device; and a catheter member extending from the handle to the delivery assembly, the catheter member having a first portion with a first compliance value and second portion with a second compliance value, the first compliance value being less than the second compliance value.

According to the present disclosure, a method for delivering a medical device into a patient may include providing a delivery device including a catheter member having a first portion with a first compliance value and a second portion with a second compliance value greater than the first compliance value; advancing the catheter member to an implant site within the patient; and at least partially releasing the medical device from a compartment adjacent the catheter member.

BRIEF DESCRIPTION OF THE DRAWINGS

Various embodiments of the present disclosure will now be described with reference to the appended drawings. It is to be appreciated that these drawings depict only some disclosed embodiments and are therefore not to be considered limiting in scope.

FIG. 3 is a perspective view of a portion of an outer catheter member of the delivery device of FIG. 1.

FIG. 4A is a cross-sectional view of a distal subassembly of the delivery device of FIG. 1.

FIGS. 6A-C are partial cut-away views of the distal subassembly of FIG. 1 at different stages of deployment.

DETAILED DESCRIPTION

As used herein, the terms "proximal" and "distal" are to be taken as relative to a user using the disclosed delivery devices. "Proximal" is to be understood as relatively close to the user and "distal" is to be understood as relatively farther away from the user. Also, as used herein, the terms "substantially," "generally," and "about" are intended to mean that slight deviations from absolute are included within the scope of the term so modified.

In traditional valve deployment methods, to facilitate translation of force from the handle of the delivery device to an end of the catheter, particularly in the distal direction, the outer sheath or inner shaft that is being translated may need to have a threshold amount of stiffness, otherwise the distal motion of the carriage may not be properly translated to the outer sheath or inner shaft. At least some of the disclosure provided herein may provide for valve deployment with limited portions of the device experiencing tension and/or compression during delivery which may allow, for example, for the use of materials with relatively high compliance.

Figure 1:
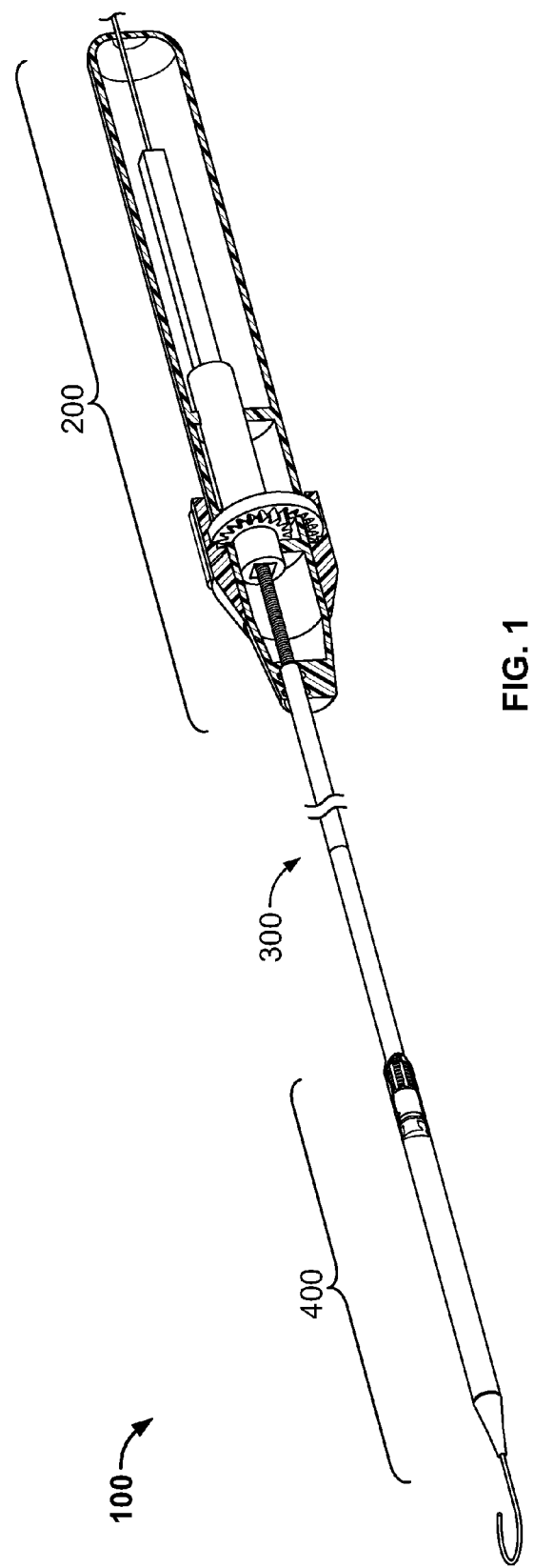
FIG. 1 is a perspective view of a delivery device according to an embodiment of the disclosure with a handle shown in a partial cut-away.

For example, referring now to FIG. 1, an exemplary transfemoral delivery device 100 for delivering a collapsible prosthetic heart valve (or other types of self-expanding collapsible stents) is illustrated. Generally, delivery device 100 includes a handle subassembly 200, an outer catheter 300, and a delivery subassembly 400, the structure and function of each of which is described in greater detail below. As is described in greater detail below, particularly in relation to FIGS. 5A-6C, the structure of delivery device 100 may limit the length of outer catheter 300 which experiences tension and/or compression forces during valve deployment, permitting the use of compliant materials in the construction of the outer catheter.

Figure 2A:
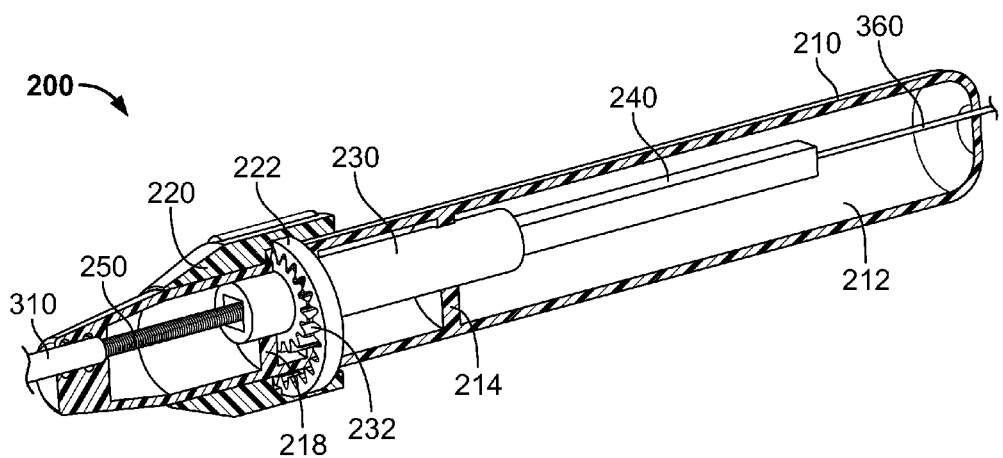
FIG. 2A is a partial cut-away view of the handle of FIG. 1.
Figure 2B:
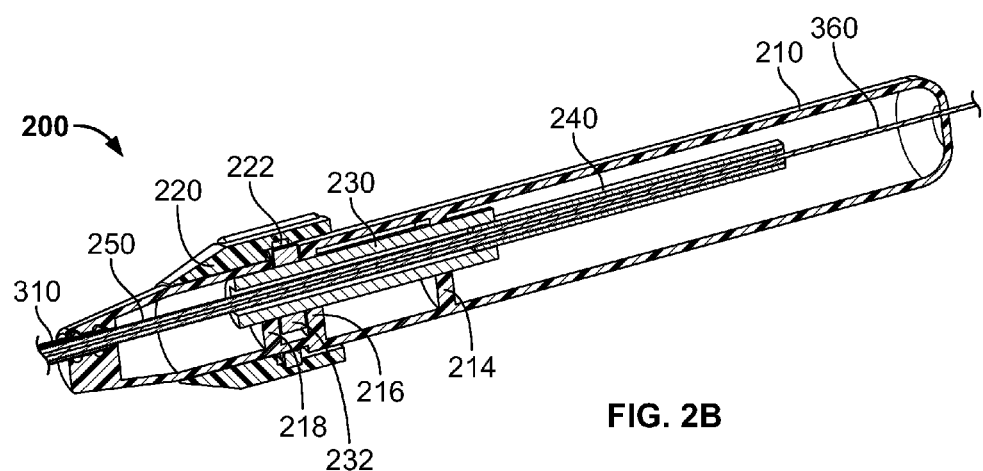
FIG. 2B is a cross-sectional view of the handle of FIG. 1.

FIGS. 2A-B show partial cutaway and cross-sectional views, respectively, of handle subassembly 200. Generally, handle subassembly 200 includes a handle housing 210, a deployment knob 220, a center drive 230, a drive key 240, and a drive screw 250.

Handle housing 210 may generally take the form of a hollow cylinder tapered at a distal end thereof. Handle housing 210 may include a first portion and a second portion, which may be individual pieces configured to be joined to one another, for example by an adhesive. The first and second portions of handle housing 210 define an elongated interior space 212, the elongated space being interrupted by first, second, and third interior walls 214, 216, 218. Interior walls 214, 216, 218 may each include an aperture in which a rotatable drive mechanism, such as center drive 230, is configured to fit.

Center drive 230 may generally take the form of an elongated cylinder with a channel extending longitudinally therethrough. In the illustrated embodiment, center drive 230 is positioned within correspondingly shaped apertures in interior walls 214, 216, 218, such that the fit is snug but the center drive is capable of rotation about its longitudinal axis. Center drive 230 may include a spur gear 232 having a plurality of teeth extending radially outward from center drive 230. Spur gear 232 may be bonded or otherwise fixedly connected to center drive 230, or may be formed integrally with the center drive as a single monolithic piece. Spur gear 232 may be positioned between interior walls 216 and 218, and may be sized so that an outer perimeter of the spur gear projects outwardly through a slot in handle housing 210.

Deployment knob 220 may generally take the form of a cylinder with a tapered distal end rotatably coupled to handle housing 210. Deployment knob 220 may include a ring gear 222 having a plurality of teeth extending radially inward from deployment knob 220. Ring gear 222 may be bonded or otherwise fixedly connected to deployment knob 220, over molded to an inner diameter of the deployment knob, or formed integrally with the deployment knob. Deployment knob 220 may be positioned on handle housing 210 such that the teeth of ring gear 222 interlock with the teeth of spur gear 232. As a result, rotation of deployment knob 220 relative to handle housing 210 will result in a corresponding rotation of center drive 230. Spur gear 232 may also extend partially into a circumferential slot on the inner diameter of deployment knob 220 to restrict the movement of the deployment knob longitudinally relative to handle housing 210. Deployment knob 220 functions as an actuation member, but it should be appreciated that other types of actuation members may provide the desired function other than a deployment knob.

Drive key 240 may generally take the general form of an elongated rectangular member with a channel formed longitudinally therethrough. Drive key 240 may have a transverse cross-section that corresponds to the transverse cross-section of the channel in center drive 230, and may be sized to fit snugly within the center drive channel. As a result, rotation of center drive 230 causes a corresponding rotation of drive key 240 and vice versa. Although the channel in center drive 230 has a generally rectangular cross-section and drive key 240 has a generally rectangular cross-section, both the channel in the center drive and the drive key may take other corresponding cross-sections, such as triangular or elliptical, which allow for transmission of torque between the members.

Lead screw 250 may take the general form of an elongated cylinder and may be, for example, a torque cable. A proximal portion of lead screw 250 may extend within and be secured to, for example by bonding or other adhesive means, the channel in drive key 240. In this configuration, torque may be transmitted between lead screw 250 and drive key 240, while axial translation of the lead screw may cause corresponding translation of the drive key. Lead screw 250 may also contain a through bore extending along its longitudinal axis configured to accept, for example, a guidewire 360 therethrough. Guidewire 360 may exit a proximal end of handle housing 210 through a proximal aperture in the handle housing. Lead screw 250 may extend through a channel in the distal end of handle housing 210 and further through outer catheter 300, described in greater detail in relation to FIG. 3. A distal portion of lead screw 250 may be threaded to interact with corresponding threading of a nut 410, such that rotation of the lead screw with respect to the nut causes axial translation of the lead screw in the proximal or distal direction, depending on the direction of rotation. The structure of nut 410 and the interaction between lead screw 250 and the nut is described in greater detail below in relation to FIGS. 4A-C.

As noted above, the distal end of handle housing 210 may include a channel through which lead screw 250 extends. Still referring to FIGS. 2A-B, a proximal end 310 of outer catheter 300 may be fixed within the channel, for example by bonding or by adhesives, such that the outer catheter is rotationally and axially fixed with respect to handle housing 210.

It should be noted that, with respect to handle subassembly 200 and components thereof, the above description pertains to the illustrated embodiment. However, a number of variations may be made to handle subassembly 200 and its components without varying from the scope of the disclosure. For example, handle housing 210 has been described as being formed of two portions. However, handle housing 210 may be formed of a single portion, or more than two portions. Further, the particular shapes and configurations of the components of handle subassembly 200 may be otherwise varied as should be apparent to one of skill in the art.

Outer catheter 300 is shown isolated in FIG. 3. Outer catheter 300 may generally take the form of an elongated hollow cylinder extending from proximal end 310 (shown in FIGS. 2A-B) to a distal end 320. Outer catheter 300 may include a plurality of different zones. For example, outer catheter 300 may include a proximal zone 330, an intermediate zone 340, and a distal zone 350. Proximal zone 330 and intermediate zone 340 may have similar or approximately equal diameters, with distal zone 350 having a greater diameter than both the proximal and intermediate zones. Proximal zone 330 and intermediate zone 340 may have different levels of stiffness or compliance. For example, proximal zone 330 may be less compliant (or more stiff) than intermediate zone 340. As is described in greater detail below with respect to FIG. 7, this configuration may facilitate the use of additional components to enhance accuracy during delivery and deployment of a prosthetic valve. Distal zone 350 may extend to and cover a portion or all of delivery subassembly 400. Specific materials that may be used to form proximal zone 330, intermediate zone 340, and/or distal zone 350 include, for example, Pebax, nylon, stainless steel braid, Vectran, polyether ether ketone (PEEK), polytetrafluoroethylene (PTFE) and nickel titanium alloys such as nitinol. Although any combination of materials may be suitable for use in proximal zone 330 and distal zone 340, in some examples materials may be chosen such that proximal zone 330 has relatively low compliance compared to intermediate zone 340 and distal zone 350.

Figure 4B:
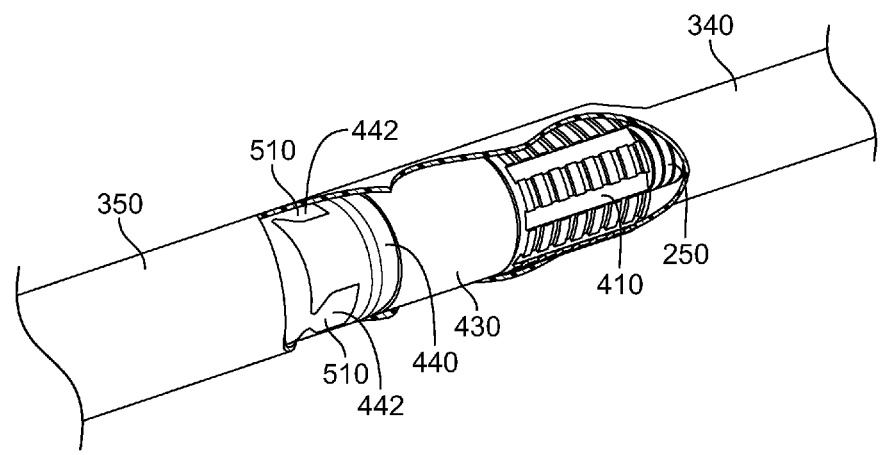
FIG. 4B is an enlarged partial cut-away view of the distal subassembly of FIG. 1.

A cross-sectional view of distal subassembly 400 is illustrated in FIG. 4A. Enlarged portions of distal subassembly 400 are illustrated in partial cutaway and cross-sectional views in FIGS. 4B-C, respectively. In the configuration illustrated in FIGS. 4A-C, distal zone 350 of outer catheter 300 surrounds many components of distal subassembly 400. Generally, distal subassembly 400 includes nut 410, an inner rotary coupling 420, an outer rotary coupling 430, a proximal hub 440, and a distal hub 450.

Nut 410 may generally take the form of a cylindrical member with internal threads configured to mate with threads on lead screw 250. The threads of nut 410 and lead screw 250 may have the same pitch. Nut 410 may be bonded, adhered, or otherwise affixed to an inner portion of distal zone 350 of outer catheter 300 such that the nut is rotationally and axially fixed with respect to the outer catheter. Nut 410 may be formed from various suitable materials, including biocompatible metals and/or plastics. Although a nut is described, other fixed internally threaded members may be used in its place. Nut 410 may also take the form of, for example, a split nut which may simplify manufacturing delivery device 100.

Inner rotary coupling 420 may take the form of a generally cylindrical hollow member with a flanged proximal base. The distal end of lead screw 250 is covered by inner rotary coupling 420, with the inner rotary coupling being bonded, adhered, or otherwise affixed to the lead screw such that the inner rotary coupling is rotationally and axially fixed with respect to the lead screw. A proximal end of inner rotary coupling 420 may include an aperture through which lead screw 250 passes, while a distal end of the inner rotary coupling may include an aperture sized to allow the passage of guidewire 360 therethrough. At least the portion of the distal end of lead screw 250 that extends into proximal hub 440 is covered by inner rotary coupling 420. In this configuration, the threads of lead screw 250 do not directly contact proximal hub 440. Rather, inner rotary coupling 420, which may have a smooth outer surface, is in contact with proximal hub 440. Inner rotary coupling 420 may be formed of a low friction material such as polyoxymethylene (e.g. acetal), PTFE, or stainless steel with a lubricant such as silicon. The distal ends of inner rotary coupling 420 and/or lead screw 250 abut an inner contact surface of proximal hub 440. In this configuration, as lead screw 250 and attached inner rotary coupling 420 are translated distally, the distal ends of the inner rotary coupling and/or lead screw push against the inner contact surface of proximal hub 440, causing the proximal hub to translate distally. This function is described in greater detail below in relation to FIGS. 5A-C and FIGS. 6A-C.

Outer rotary coupling 430 may take the form of a generally cylindrical hollow member having a generally flat proximal end and a shaped distal end. The flat proximal end of outer rotary coupling 430 may include an aperture configured to allow passage of lead screw 250 therethrough. The distal end of outer rotary coupling 430 may be sized and shaped to mate with the shape of a proximal end of proximal hub 440. For example, if the proximal end of proximal hub 440 is generally convex, the distal end of outer rotary coupling 430 may be concave. These mating shapes may facilitate the fixation of outer rotary coupling 430 to a proximal end of proximal hub 440, through bonding, adhesives, or other means of affixation. In this configuration, outer rotary coupling 430 is axially and rotationally fixed with respect to proximal hub 440, but may translate axially with respect to outer catheter 300. Outer rotary coupling 430 may be formed of a low friction material such as polyoxymethylene (e.g. acetal), PTFE, or stainless steel with a lubricant such as silicon.

As noted above, inner rotary coupling 420 may include a flanged proximal base. This flanged proximal base may abut a contact surface of outer rotary coupling 430. The flanged proximal base may provide an increased surface area of contact between the proximal end of inner rotary coupling 420 and the contact surface of outer rotary coupling 430. The flanged base may also keep inner rotary coupling 420 centered in outer rotary coupling 430 while minimizing rotational friction between the two. As lead screw 250 and attached inner rotary coupling 420 are translated proximally, the flanged base of the inner rotary coupling forces outer rotary coupling 430 proximally. Because outer rotary coupling 430 is fixed to proximal hub 440, the proximal hub is also translated proximally as a result of the above-described motion. This is described in more detail in relation to FIGS. 5A-C and FIGS. 6A-C.

Figure 4C:
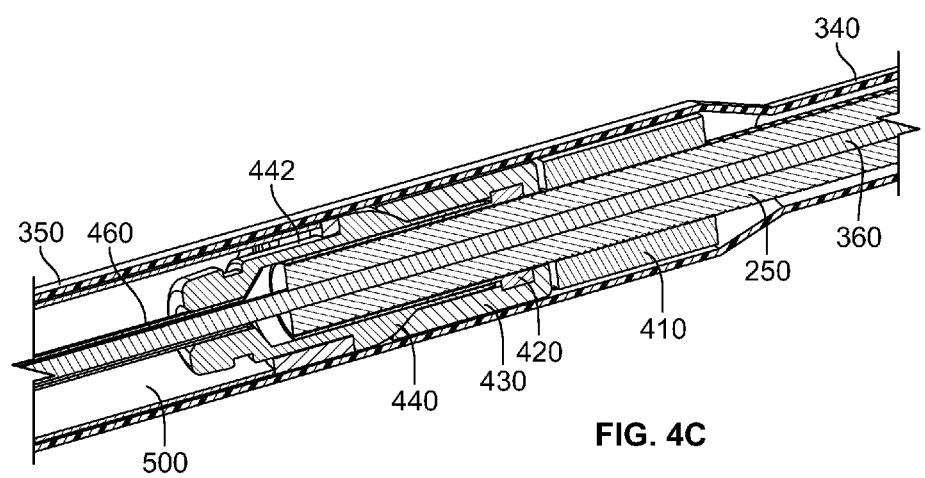
FIG. 4C is an enlarged partial cross-sectional view of the distal subassembly of FIG. 1.

Still referring to FIGS. 4A-C, proximal hub 440 and distal hub 450 may be connected by an inner shaft 460. Inner shaft 460 may be a generally cylindrical hollow member configured to transmit axial motion of proximal hub 440 to distal hub 450. Inner shaft 460 may be integrally formed with proximal hub 440 and distal hub 450, or may be otherwise affixed to the proximal and distal hubs. Inner shaft 460 may be sized to allow passage of guidewire 360 therethrough.

In combination, proximal hub 440, distal hub 450, inner shaft 460, and the distal zone 350 of outer catheter 300 define a compartment C in which a collapsible and expandable medical device, such as prosthetic heart valve 500, may be stored in a collapsed configuration during delivery. It should be noted that, although collapsible prosthetic heart valve 500 is depicted herein as a unitary solid member for clarity of illustration, a typical prosthetic heart valve would take the form of a prosthetic valve mounted on a stent that is formed of a number of interconnecting struts. Proximal hub 440 may include one or more retention features, such as cut-outs 442, having a trapezoidal, circular, or other shape corresponding to the shape of retention features 510 extending from the aortic end of prosthetic valve 500. During delivery, retention features 510 of prosthetic valve 500 are positioned within cut-outs 442 and, as long as the distal zone 350 of outer catheter 300 is positioned over the cut-outs, the prosthetic valve remains connected to delivery device 100. As is described in greater detail below with respect to FIGS. 6A-C, this configuration allows prosthetic valve 500 to be resheathed back into compartment C after its partial release.

Distal hub 450 may take the general form of a cylindrical body that tapers to an atraumatic tip 452 at a distal end. A proximal end of distal hub 450 may also be slightly tapered in the proximal direction, which may help the annulus end of prosthetic heart valve 500 to sit within compartment C more securely. Distal hub 450 may also include a channel therethrough sized and configured to allow passage of guidewire 360 through the channel.

In an exemplary aortic valve replacement procedure, prosthetic heart valve 500 is loaded within compartment C of distal subassembly 400, with retention features 510 of the prosthetic valve positioned within cut-outs 442 of proximal hub 440 and distal zone 350 of outer catheter 300 entirely covering the collapsed prosthetic valve. An incision is made in the patient at the point of intended entry which may be, for example, through the femoral artery. If desired, guidewire 360 may be inserted into the incision and guided to the implant site. If guidewire 360 is used, delivery device 100 may be threaded over the guidewire to facilitate advancement of the delivery device to the implant site. Delivery device 100 is advanced through the vasculature and around the aortic arch until delivery subassembly 400 is positioned at or near the position of the native valve annulus. Once the surgeon confirms that delivery subassembly 400 is in a desired position for releasing prosthetic valve 500, handle subassembly 200 may be operated to deploy the prosthetic valve. Prior to beginning deployment of prosthetic valve 500, handle subassembly 200 is at an initial position with drive key 240 at a proximalmost position, as illustrated in FIGS. 2A-B, and distal zone 350 of outer catheter 300 completely covering the collapsed prosthetic valve, as illustrated in FIG. 4A.

Figure 5A:
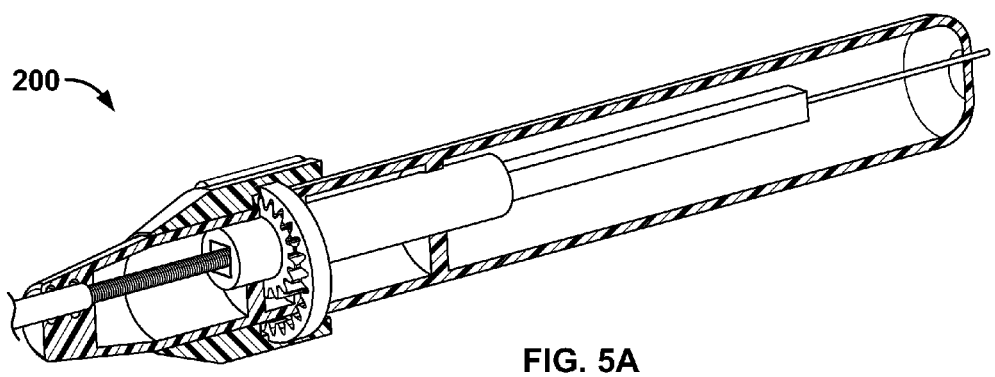
FIGS. 5A-C are partial cut-away views of the handle of FIG. 1 at different stages of deployment.
Figure 5B:
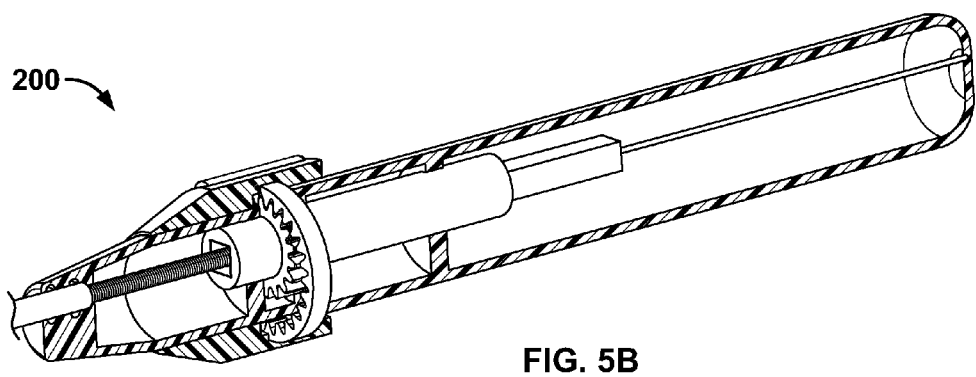
Figure 5C:
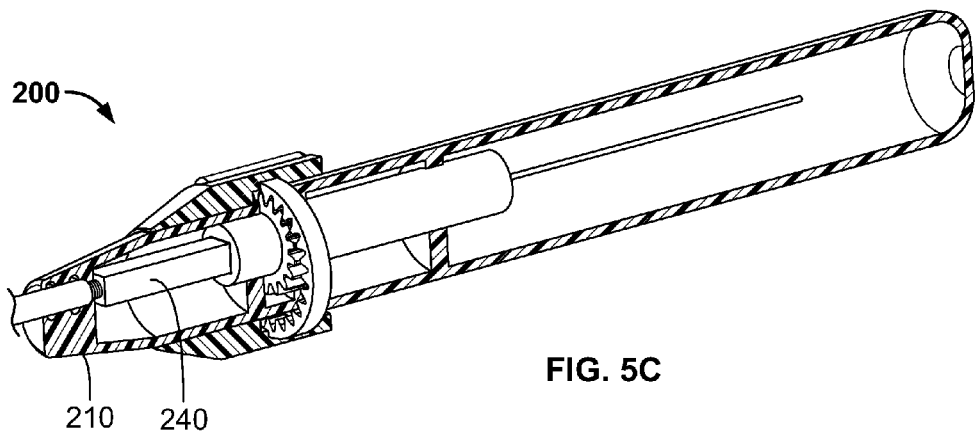

Handle subassembly 200 is illustrated in FIGS. 5A-C in incremental stages of deployment. To begin deployment, the user rotates deployment knob 220 in a first direction, causing spur gear 232 to rotate along with ring gear 222, which in turn causes center drive 230, drive key 240, and lead screw 250 to all rotate. As the external threads of lead screw 250 rotate in engagement with the internal threads of nut 410, the lead screw is pulled distally. The distal ends of lead screw 250 and/inner rotary coupling 430 push against the inner contact surface of proximal hub 440, causing the proximal hub and, hence, distal subassembly 400, to move distally as well. Because of the configuration of inner rotary coupling 420 and outer rotary coupling 430, only axial motion, and not rotational motion, of lead screw 250 is translated to proximal hub 440. Further, because lead screw 250 is pulled distally due to the rotation of its threads relative to internal threads of nut 410, the entire outer catheter 300 does not need to be stiff enough to easily transmit axial force along its entire length. In one embodiment, the distal zone 350 of outer catheter 300 may be about 3 inches (7.62 cm) long. In this embodiment, only about 3 inches (7.62 cm) of the distal end of lead screw 250 is in tension and/or compression during advancement and/or retraction. FIGS. 5A, 5B, and 5C illustrate handle subassembly 200 after an initial increment of deployment, an intermediate increment of deployment, and full deployment, respectively. In the current example, FIG. 5A represents about 0.375 inches (0.95 cm) of deployment, FIG. 5B represents about 1.5 inches (3.81 cm) of deployment, and FIG. 5C represents about 3 inches (7.6 cm) of deployment. It should be noted that drive key 240 contacts a distal end of handle housing 210, which provides a limit as to how far the drive key may travel in the distal direction. The 3 inch length of distal zone 350 of outer catheter 300 is merely illustrative of one possible embodiment. Those of skill in the art should understand that different lengths may be appropriate under different circumstances.

Distal subassembly 400 is illustrated in FIGS. 6A-C at positions corresponding to those illustrated in FIGS. 5A-C. It should be noted that in FIGS. 6A-C, distal zone 350 of outer catheter 300 is shown in a partial cutaway view to illustrate the components positioned within the distal zone. At the initial increment of deployment, illustrated in FIG. 6A, the annulus end of prosthetic valve 500 begins to extend beyond the distal end of distal zone 350 of outer catheter 300 and begins to expand (expansion not illustrated in FIGS. 6A-C).

At the intermediate increment of deployment (shown in FIG. 6B), about half of prosthetic valve 500 extends beyond distal zone 350 of outer catheter 300. At the initial and intermediate increments of deployment, and at any time before full deployment, the retention features 510 of prosthetic valve 500 are trapped within cut-outs 442 of proximal hub 440 and covered by a portion of distal zone 350 of outer catheter 300. As long as retention features 510 remain in this position, despite the fact that portions of prosthetic valve 500 may have already expanded, the prosthetic valve may be resheathed within distal zone 350 of outer catheter 300 by rotating deployment knob 220 in the opposite direction. The user may desire to resheath prosthetic valve 500 if, for example, it is determined that the placement of the prosthetic valve is not desirable.

Distal subassembly 400 at full deployment is illustrated in FIG. 6C. At this point, prosthetic valve 500 is fully expanded at the implant site and cannot be resheathed. The user may rotate deployment knob 220 in the opposite direction to pull distal subassembly 400 proximally back into distal zone 350 of outer catheter 350. Because of the configuration of inner rotary coupling 420 and outer rotary coupling 430, and in particular the flanged base of the inner rotary coupling, proximal movement of lead screw 250 causes proximal movement of proximal hub 440. As noted above in relation to FIGS. 4A-C, as lead screw 250 and attached inner rotary coupling 420 are pulled proximally, the flanged base of the inner rotary coupling presses against the contact surface of outer rotary coupling 430, which is fixed to proximal hub 440. In this configuration, proximal movement of lead screw 250 results in proximal movement of proximal hub 440. Once distal subassembly 400 is fully positioned within distal zone 350 of outer catheter 300, the user may remove delivery device 100 and guidewire 360 from the patient, completing the procedure.

Figure 7:
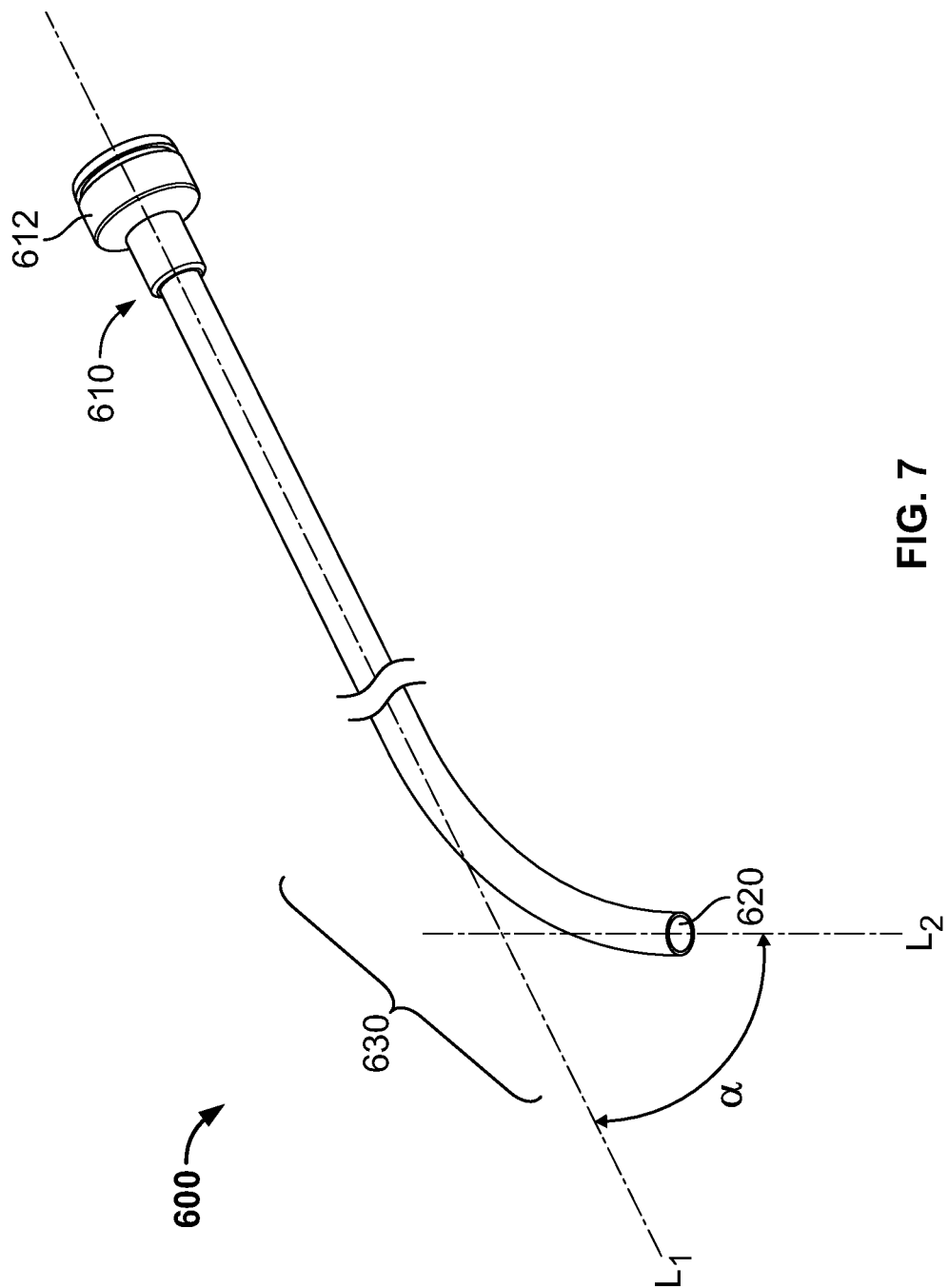
FIG. 7 is a perspective view of an overlying sheath for use with the delivery device of FIG. 1.

In another embodiment of the disclosure, an overlying sheath 600, illustrated in FIG. 7, may be used along with delivery device 100 to increase the accuracy with which the distal end of the delivery device is placed at the implant site. Overlying sheath 600 may take the general form of an elongated hollow cylinder extending from a proximal end 610 to a distal end 620. Proximal end 610 may include an introducer hub 612. A distal portion 630 of overlying sheath 600 may be pre-shaped such that the distal portion is angled with respect to the remainder of the overlying sheath. For example, distal portion 630 may be smoothly curved as illustrated or otherwise angled, such as having an abrupt bend. In this configuration, overlying sheath 600 takes the form illustrated in FIG. 7 when no force is applied to the overlying sheath. In particular, a proximal portion of overlying sheath 600 may extend along a first longitudinal axis $L_1$, while distal end 620 of distal portion 630 extends along a second longitudinal axis $L_2$. First longitudinal axis $L_1$ may form an angle α with respect to second longitudinal axis $L_2$.

In use, overlying sheath 600 may be placed over delivery device 100 prior to insertion into the patient, with distal end 620 of the overlying sheath being positioned at, or just proximal of, the point of transition between proximal zone 330 and intermediate zone 340 of outer catheter 300. Overlying sheath 600 may be formed of a material such as Pebax, nylon, stainless steel braid, PEEK, Vectran, PTFE, or nitinol. The chosen material may have greater compliance than proximal zone 330 of outer catheter 300 but lower compliance than intermediate zone 340 of the outer catheter. In this configuration, during advancement of delivery device 100 as described in relation to FIGS. 5A-6C, overlying sheath 600 remains in a position over proximal zone 330 of outer catheter 300 during the majority of delivery, until the distal end of the delivery device is at or near the aortic arch. Because overlying sheath 600 is more compliant than proximal zone 330 of outer catheter 300, the overlying sheath takes the form of the proximal zone of the outer catheter. However, once at or near the aortic arch, overlying sheath 600 may be advanced distally. As the pre-shaped distal portion 630 of overlying sheath 600 advances from the less compliant proximal zone 330 to the more compliant intermediate zone 340 of outer catheter 300, the pre-shaped distal portion reverts to its pre-formed shape. As it does so, it will cause intermediate zone 340 to bend to substantially the same shape. This pre-formed shape may help center distal subassembly 400 within the native annulus, which otherwise may be difficult because of the shape of the aortic arch.

In the illustrated embodiment, angle α between first longitudinal axis $L_1$ and second longitudinal axis $L_2$ is about 45°, but other angles may be desirable. For example, angle α may be between about 15° and about 75°, between about 30° and about 60°, between about 35° and about 55°, or between about 40° and about 50°. Further, in the illustrated embodiment, distal portion 630 is about 1 inch (2.54 cm) long, but other lengths may be desirable. For example, distal portion 630 may be about 0.5 inches (1.27 cm) long, about 1.5 inches (3.81 cm) long, about 2 inches (5.08 cm) long, about 3 inches (7.62 cm) long, about 4 inches (10.16 cm) long, about 5 inches (12.7 cm) long, about 6 inches (15.24 cm) long, or any length between about 0.5 inches (1.27 cm) and 6 inches (15.24 cm).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. It will be appreciated that the various dependent claims and the features set forth therein can be combined in different ways than presented in the initial claims. It will also be appreciated that the features described in connection with individual embodiments may be shared with others of the described embodiments.

According to one embodiment of the present disclosure, a delivery device for a collapsible medical device may include a handle having an actuation member; a delivery assembly having a compartment for receiving the medical device; a catheter member extending from the handle to the delivery assembly; an internally threaded member fixedly connected to the delivery assembly; and an externally threaded member having a first portion operatively connected to the actuation member and a second portion threadedly coupled to the internally threaded member so that manipulation of the actuation member causes axial movement of the compartment relative to the catheter member; and/or the delivery assembly may further comprise a first hub connected at a spaced distance to a second hub, the externally threaded member being operatively connected to the first hub; and/or the delivery device may further comprise a rotary coupling interposed between the externally threaded member and the first hub; and/or the rotary coupling may include a first portion fixedly connected to the externally threaded member and a second portion fixedly connected to the first hub, the first portion being rotatable relative to the second portion; and/or manipulation of the actuation member may cause axial movement of the first hub but may not cause substantial rotational movement of the first hub.

According to another embodiment of the present disclosure, a delivery device for a collapsible medical device may include a handle; a delivery assembly having a compartment for receiving the medical device; and a catheter member extending from the handle to the delivery assembly and having a first portion with a first compliance value and a second portion with a second compliance value, the first compliance value being less than the second compliance value; and/or the first portion may be positioned proximally relative to the second portion; and/or the delivery device may further comprise a sheath having a proximal portion and a distal portion, the sheath being configured to be positioned at least partially over the catheter member, a longitudinal axis of the proximal portion is disposed at an acute angle with respect to a longitudinal axis of the distal portion when no force is applied to the sheath; and/or the sheath may have a third compliance value between the first compliance value and the second compliance value; and/or the angle between the longitudinal axis of the proximal portion of the sheath and the longitudinal axis of the distal portion of the sheath may be between about 15° and about 75°; and/or the angle between the longitudinal axis of the proximal portion of the sheath and the longitudinal axis of the distal portion of the sheath may be between about 35° and about 55°; and/or the angle between the longitudinal axis of the proximal portion of the sheath and the longitudinal axis of the distal portion of the sheath may be about 45°.

According to the present disclosure, a method for delivering a medical device into a patient may include providing a delivery device including a catheter member having a first portion with a first compliance value and a second portion with a second compliance value greater than the first compliance value; advancing the catheter member to an implant site within the patient; and at least partially releasing the medical device from a compartment adjacent the catheter member; and/or the method may further include positioning a sheath at least partially over the catheter member, the sheath having a distal portion that is disposed at an acute angle with respect to a remainder of the sheath when no force is applied to the sheath; and/or prior to the advancement step, the distal portion of the sheath may be positioned over the first portion of the catheter member so that the distal portion of the sheath is not disposed at an acute angle with respect to the remainder of the sheath; and/or the method may further comprise distally advancing the sheath with respect to the catheter member prior to the releasing step so that the distal portion of the sheath is positioned over the second portion of the catheter member; and/or the step of distally advancing the sheath may cause the distal portion of the sheath to be disposed at an acute angle with respect to the remainder of the sheath; and/or the method may further comprise centering the compartment within a native valve annulus of the patient prior to at least partially releasing the medical device; and/or the delivery device may further comprise a handle having an actuation member and a delivery assembly at least partially defining the compartment; and/or the delivery device may further include an internally threaded member fixedly connected to the delivery assembly and an externally threaded member having a first portion operatively connected to the actuation member and a second portion threadedly coupled to the internally threaded member, wherein the releasing step may include rotating and axially advancing the externally threaded member.

The invention claimed is:

1. A delivery device for a collapsible medical device, the delivery device comprising:
   a handle having an actuation member;
   a distal catheter portion for receiving the medical device;
   a catheter member extending from the handle to the distal catheter portion, the catheter member fixedly coupled to the distal catheter portion;
   an internally threaded member fixedly connected to the distal catheter portion so that the internally threaded member is rotationally and translationally fixed with respect to the distal catheter portion;
   a first hub fixedly connected to a second hub at a spaced distance, the first hub adapted to contact the collapsible medical device when the collapsible medical device is received within the distal catheter portion;
   an externally threaded member having a first portion operatively connected to the actuation member and a second portion threadedly coupled to the internally threaded member so that manipulation of the actuation member causes axial movement of the distal catheter portion relative to the first hub, and
   a rotary coupling having a first portion translationally and rotationally fixed to the externally threaded member, and a second portion translationally and rotationally fixed to the first hub, the first portion being rotatable relative to the second portion and translationally fixed relative to the second portion,
   wherein the externally threaded member extends through a distal end of the handle and through substantially an entire length of the catheter member.

2. The delivery device according to claim 1, wherein manipulation of the actuation member causes axial movement of the first hub but does not cause substantial rotational movement of the first hub.

3. A delivery device for a collapsible medical device, the delivery device comprising:
   a handle;
   a catheter member extending from a proximal end fixedly coupled to the handle to a distal end, the catheter member having a proximal portion with a first compliance value, a distal portion at the distal end for receiving the medical device in a collapsed condition, and an intermediate portion positioned between the proximal portion of the catheter member and the distal portion of the catheter member, the intermediate portion of the catheter member having a second compliance value, the first compliance value being less than the second compliance value; and
   a sheath having a proximal portion and a distal portion, the sheath being configured to be positioned over both the proximal portion of the catheter member and the intermediate portion of the catheter member, a longitudinal axis of the proximal portion of the sheath being disposed at an acute angle with respect to a longitudinal axis of the distal portion of the sheath when no force is applied to the sheath, the sheath having a third compliance value between the first compliance value and the second compliance value.

4. The delivery device according to claim 3, wherein the angle between the longitudinal axis of the proximal portion of the sheath and the longitudinal axis of the distal portion of the sheath is between about 15° and about 75°.

5. The delivery device according to claim 3, wherein the angle between the longitudinal axis of the proximal portion of the sheath and the longitudinal axis of the distal portion of the sheath is between about 35° and about 55°.

6. The delivery device according to claim 3, wherein the angle between the longitudinal axis of the proximal portion of the sheath and the longitudinal axis of the distal portion of the sheath is about 45°.

7. The delivery device according to claim 3 wherein, in an assembled condition of the delivery device, the sheath is slidable relative to the catheter member.

8. The delivery device according to claim 3, wherein the distal portion of the catheter member has an outer diameter that is larger than an outer diameter of the intermediate portion of the catheter member.

* * * * *